United States Patent [19]
Kohnen et al.

[11] Patent Number: 5,405,339
[45] Date of Patent: Apr. 11, 1995

[54] MEDICAL CONNECTOR AND METHOD FOR CONNECTING MEDICAL TUBING

[75] Inventors: Jane L. Kohnen, Minneapolis; Jeffry C. Palm, Coon Rapids; Roger L. Struve, Shoreview, all of Minn.

[73] Assignee: Medtronic, Inc., Minneapolis, Minn.

[21] Appl. No.: 117,386

[22] Filed: Sep. 3, 1993

[51] Int. Cl.$^6$ ............................................. A61M 25/00
[52] U.S. Cl. ...................................... 604/283; 604/905
[58] Field of Search ...................... 604/7, 29, 93, 174, 604/283, 905; 285/169, 176, 177

[56] References Cited

U.S. PATENT DOCUMENTS

| | | | |
|---|---|---|---|
| 4,226,815 | 5/1981 | Cross | 285/330 |
| 4,253,684 | 3/1981 | Tolbert et al. | 604/905 |
| 4,334,551 | 6/1982 | Pfister | 137/614.03 |
| 4,479,796 | 10/1984 | Kallok | 604/175 |
| 4,511,163 | 4/1985 | Harris et al. | 604/283 |
| 4,526,572 | 7/1985 | Donnan et al. | 604/29 |
| 4,650,473 | 3/1987 | Bartholemew et al. | 604/174 |
| 4,693,707 | 9/1987 | Dye | 604/905 |
| 4,745,950 | 5/1988 | Mathieu | 137/798 |
| 4,778,447 | 10/1988 | Velde et al. | 604/29 |
| 4,790,832 | 12/1988 | Lopez | 604/283 |
| 4,994,048 | 2/1991 | Metzger | 604/283 |
| 5,057,074 | 10/1991 | Suzuki et al. | 604/29 |
| 5,092,849 | 3/1992 | Sampson | 604/283 |
| 5,098,395 | 3/1992 | Fields | 604/168 |
| 5,139,483 | 8/1992 | Ryan | 604/86 |
| 5,205,821 | 4/1993 | Kruger et al. | 604/283 |

FOREIGN PATENT DOCUMENTS 2949315  7/1980  Germany ............................ 604/93

OTHER PUBLICATIONS

Medtronic Synchromed Infusion System, Model 8703B Intraspinal Catheter, Technical Manual, Jul. 1992.
Shiley Infusaid, Inc., Catheter Connector, Photocopy of Connector at 2x magnification, pump specification and accessory specification, pp. 1, 13, 1x. Copyright 1988.
Du Pen Catheter Connector, as represented by photocopy of connector at 2x magnification.

*Primary Examiner*—C. Fred Rosenbaum
*Assistant Examiner*—Frank Wilkens, III
*Attorney, Agent, or Firm*—Terry L. Wiles; Harold R. Patton

[57] ABSTRACT

A medical connector and method of using the connector to connect separate sections of medical tubing, especially tubing which is to be implanted in the human body. The connector includes generally cylindrical first and second end portions, the diameter of which are smaller than an enlarged middle portion. The end portions are sized to fit within the lumens of the tubing sections. The connection is made by grasping the enlarged middle portion and slipping each end portion into a respective tubing section until the tubing sections abut tubing stop surfaces located at each end of the enlarged middle portion. The enlarged middle portion makes the connector easy to handle and the tubing stop sections provide for accurate alignment of the connector between the tubing sections.

8 Claims, 2 Drawing Sheets

MEDICAL CONNECTOR AND METHOD FOR CONNECTING MEDICAL TUBING

FIELD OF THE INVENTION

This invention relates to medical connectors used for connecting medical tubing. More particularly, the invention is directed to a medical connector for connecting sections of a catheter.

BACKGROUND OF THE INVENTION

In numerous medical applications it becomes necessary to connect one section of tubing to another. In such situations it is important that the connection be secure so that it will not pull apart and that there be no leakage of fluid at the site of the connection. This is especially critical in applications where the tubing sections are implanted in the human body.

One such application involves the use of an implantable drug pump. Such pumps are useful in the treatment of cancer pain, to control spasticity and other applications where it is desirable to provide drugs or fluid medication to a particular location in the body. A typical implant procedure involves implanting the drug pump in a body cavity or subcutaneous pocket location for delivery of drugs to the epidural space or intrathecal space of the spinal column. In this application a catheter having multiple body sections including a thin-walled distal section and a thicker-walled proximal section is used to deliver the drug to the site of administration. The distal section of the catheter is positioned in the desired location and then connected to the proximal section of the catheter by use of a medical connector. The connection is made by inserting one end of the connector into the lumen of one catheter section and the other end of the connector into the lumen of the other catheter section and then sliding the catheter sections toward the middle of the connector until they meet. The proximal section is then connected to the drug pump.

Numerous difficulties have been encountered in the manufacture and use of prior art medical connectors to connect catheter tubing sections. For example, these connectors, which have been sized to fit within the lumens of the catheter tubing sections, are very small and difficult for the implanting physician to handle. In addition, because such connectors fit entirely within the lumens of the catheter sections it is difficult for the physician to be sure that the joint between catheter sections is positioned over the center of the connector. Misalignment of the connector can result in a weakened connection which is more likely to come apart or to leak. Therefore, it would be desirable to provide a connector which is easier for the physician to handle and which prevents misalignment of the connector.

SUMMARY OF THE INVENTION

In accordance with the present invention there is disclosed a connector for connecting sections of medical tubing and a method for using the connector. The connector is shaped in a manner which solves the problems associated with prior art connectors. Specifically, the connector has an enlarged middle portion between first and second end portions. The end portions have a smaller diameter than the enlarged middle portion and are adapted to be inserted into the ends of the medical tubing sections. The connector is easier to handle than prior art connectors since it can be grasped at the enlarged middle portion. Thus, the process of inserting the end portions into the tubing sections is simplified. Additionally, the opposing edges of the enlarged middle portion act as tubing stop surfaces which provide a positive indication that the connector is properly aligned.

In one embodiment the invention is a connector for medical tubing comprising a first end portion for insertion in a section of medical tubing, a second end portion for insertion in another section of medical tubing, and an enlarged middle portion lying between the first and second end portions. The enlarged middle portion has a first tubing stop section adjacent the first end portion and a second tubing stop section adjacent the second end portion. The first and second end portions and the enlarged middle portion define a central lumen. Preferably, the first and second end portions are generally cylindrical and include an axially tapered end section to facilitate insertion in the medical tubing. The first and second end portions may advantageously include means for securing the medical tubing to the connector. The means for securing may include at least one circumferentially raised ridge or at least one circumferentially depressed section.

In another embodiment the invention is a connector for connecting catheter body sections. In this embodiment the connector comprises first and second substantially cylindrical end portions for insertion into separate catheter body sections. The connector includes an enlarged middle portion lying between the first and second end portions and having a first catheter stop section adjacent the first end portion and a second catheter stop section adjacent the second end portion. The first and second end portions and the enlarged middle portion define a central lumen through the connector which is substantially parallel to the longitudinal axis of the connector. The central lumen allows fluids to pass between the catheter body sections through the connector. Preferably, the first and second end portions each include an axially tapered end section to facilitate insertion in the catheter body sections. The first and second end portions may include means for securing the catheter body sections to the connector. This means for securing may include at least one circumferentially raised ridge or at least one circumferentially depressed section. Optionally, the connector may include a substantially circumferential groove around the enlarged middle portion which may be used for anchoring the connector to tissue with sutures.

In a further embodiment the invention is a method of connecting separate catheter sections. The method comprises inserting a substantially cylindrical first end portion of the connector into the lumen of a first catheter section. A second substantially cylindrical end portion of the connector is inserted into the lumen of a second catheter section. The first and second end portions are slid into the first and second catheter sections until the sections abut against first and second catheter stop surfaces of an enlarged middle portion of the connector lying between the first and second end portions. The first and second end portions may each include an axially tapered end section to facilitate insertion in the catheter sections. Additionally, the first and second end portions may include means for securing the catheter sections to the connector. The means for securing may include at least one circumferentially raised ridge or at least one circumferentially depressed section. Optionally, the middle portion of the connector includes a substantially circumferential groove to allow the connector to be sutured to surrounding tissue.

BRIEF DESCRIPTION OF THE DRAWINGS

The foregoing and other aspects of the present invention will be best appreciated with reference to the detailed description of the invention, which follows, when read in conjunction with the accompanying drawings wherein.

DETAILED DESCRIPTION OF THE INVENTION

Figure 1:
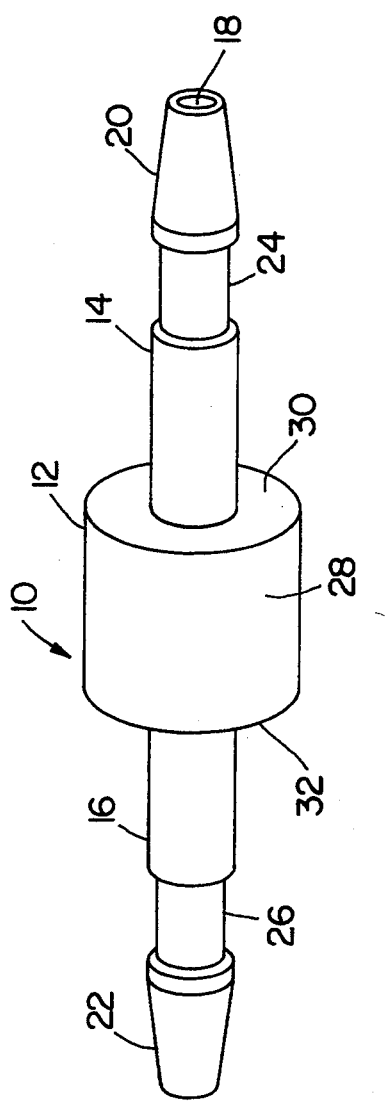
FIG. 1 is a perspective view of a medical connector in accordance with the present invention.

FIG. 1 is a perspective view of a medical connector 10 used to connect sections of medical tubing in accordance with the present invention. Medical connector 10 generally comprises an enlarged middle portion 12 located between a first end portion 14 and a second end portion 16. Connector 10 may be made of any biocompatable material including various metals and plastics, for example, titanium. A central lumen 18 extends through the connector. Lumen 18 is generally concentric to the longitudinal axis of the connector. In the embodiment shown in FIG. 1 end portions 14 and 16 include axially tapered end sections 20 and 22, respectively. Tapered end sections 20 and 22 make it easier for the connector to be inserted into the ends of the medical tubing.

Figure 4:
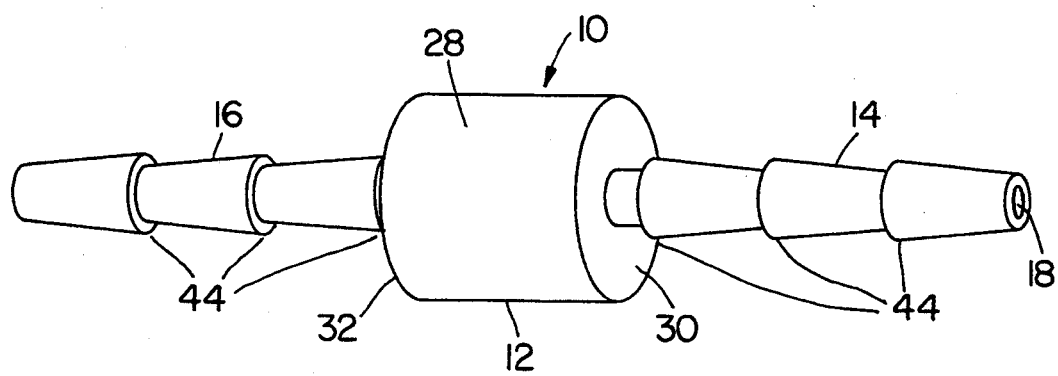
FIGS. 4 and 5 are perspective views of additional alternative embodiments of the medical connector of the present invention.
Figure 5:
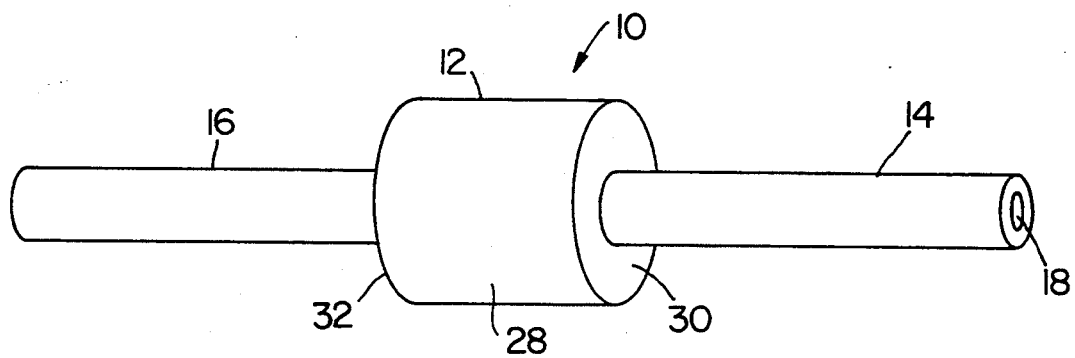

In the embodiment shown in FIG. 1 end portions 14 and 16 also include at least one circumferentially depressed section 24 and 26, respectively. Circumferentially depressed sections 24 and 26 each comprise a means for securing the medical tubing to the end portions of the connector after they have been inserted into the tubing. Since medical tubing is made of generally compliant material the inner surface of the tubing will generally comply with the surface of the end portions of the connector including the depressed sections, especially if the tubing over the end portions is ligated. Other means for securing the medical tubing to the end portions of the connector are shown in FIGS. 4 and 5 which are described in more detail hereafter.

End portions 14 and 16 are generally cylindrically shaped to comply with the shape of the lumen of the medical tubing into which they will be inserted. Although enlarged middle portion 12 is not inserted in the lumen of the medical tubing and may, therefore, be of any desired shape, a cylindrical shape as illustrated in the drawing figures has been found to be particularly advantageous.

With continued reference to FIG. 1, it can be seen that enlarged middle portion 12 comprises a generally cylindrical outer surface 28 flanked by tubing stop surfaces 30 and 32 which are generally perpendicular to the longitudinal axis of the connector. The entire connector may be of integral construction or the enlarged middle portion may be made of a secondary material which may, for example, be molded to the rest of the connector. Tubing stop surfaces 30 and 32 provide a positive stop against which the ends of the tubing abut when the connector is inserted. This allows the physician to know with confidence that the connector is properly aligned with the tubing.

Figure 2:
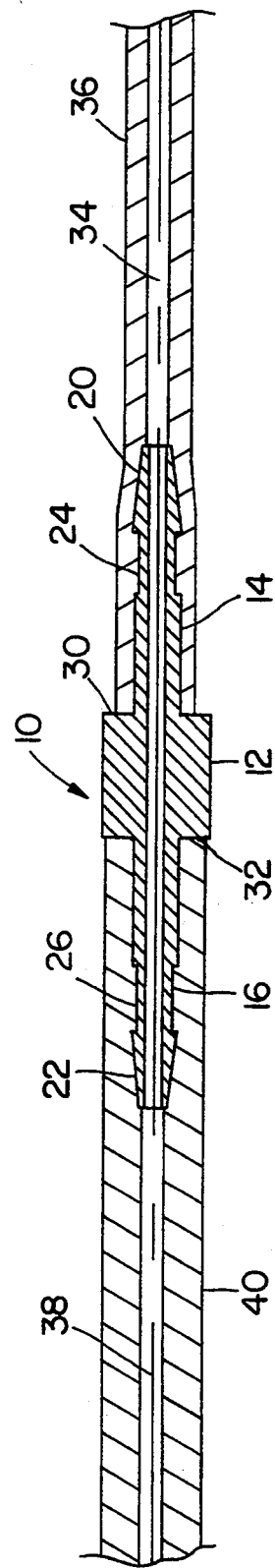
FIG. 2 is a side view in section of a connection between the distal and proximal sections of a catheter using the medical connector of FIG. 1.

The use of the connector can be understood with reference to FIG. 2 which is a side view in section of the connection of the distal and proximal sections of a catheter using the medical connector shown in FIG. 1. By way of example the use will be described with respect to the delivery of drugs or fluid medication from an implanted drug pump to the epidural space of the spinal column. It should be understood, however, that the connector of this invention may be used in any application where it is necessary to connect sections of medical tubing to one another in a secure manner.

In a spinal catheterization procedure where the catheter is to be placed in the epidural space for administration of drugs or fluid medication from an implanted drug pump the procedure begins by the placement of the distal catheter section. This section of the catheter may be inserted in the epidural space percutaneously by use of a Touhy needle in a manner known to those skilled in the art. After proper placement of the distal section of the catheter has been verified an incision is made at the needle site. A subcutaneous pump pocket is prepared at a desired location. The proximal section of the catheter is then tunneled from the site of the incision to the pump pocket. At this point in the procedure the distal and proximal catheter sections are connected using the connector of this invention.

As seen in FIG. 2, one of the end portions of connector 10, in this case end portion 14, is inserted into the lumen 34 of distal catheter section 36. The other end portion, in this case end portion 16, is inserted into the lumen 38 of proximal catheter section 40. The end portions of the connector are slid into the catheter sections until they come into contact with and abut against tubing stop surfaces 30 and 32. In practice the implanting physician makes the connection by grasping the enlarged middle section 12 and inserting one end portion into the lumen of a catheter section until further movement of the catheter over the connector is prevented by the tubing stop surface. The other end portion of the connector is inserted in the other catheter section in a similar manner. Axially tapered end sections 20 and 22 facilitate the insertion of the connector into the lumens of the catheter sections.

The advantage of using the connector of this invention is that the enlarged middle portion gives the physician a surface large enough to simplify handling of the connector while making the connection. Additionally, the tubing stop surfaces on each side of the enlarged middle portion make it virtually impossible to misalign the connector between the tubing sections. In contrast, prior art connectors used in this application have been made small enough so that the entire connector fits within the lumen of the catheter sections. Consequently, they are difficult to handle and misalignment is a problem since it is difficult for the physician to gauge whether more of the connector has been inserted into one of the catheter sections than the other. Such misalignment can compromise the integrity of the connection.

As illustrated in FIG. 2, the outer diameter of end portions 14 and 16 is slightly larger than the dimension of the of the lumens of the catheter sections. This helps to secure the catheter sections to the connector and to ensure that fluid flowing from the drug pump through lumens 38, 18 and 34 will not leak at the site of the connection. In the embodiment shown, circumferentially depressed sections 24 and 26 are included to further secure the catheter sections to the end portions of the connector. Since the catheter tubing sections are compliant they tend to conform to the shape of the depressed sections and make it less likely that the catheter sections will slip off of the end portions of the connector. The connection between the catheter sections and the connector may be further secured by ligating the catheter section over each end portion of the connector.

Optionally, a strain relief sleeve may be used to further strengthen the connection. Although not shown in the drawing the sleeve is slipped over one of the catheter sections before the connection is made. Once the connector has been inserted into both catheter sections the sleeve is slipped over the connection joint and ligated on both sides of the enlarged middle portion.

The size of medical connector 10 depends upon the size of the medical tubing which is being connected. For example, in the application just described, the inner diameter of the catheter tubing sections is approximately 0.021 inch and the outer diameter of the end portions is approximately 0.038 inch. The outer diameter of enlarged middle portion 12 is approximately 0.092 inch while the outer diameter of the distal and proximal catheter tubing sections are approximately 0.055 inch and 0.085 inch, respectively.

Figure 3:
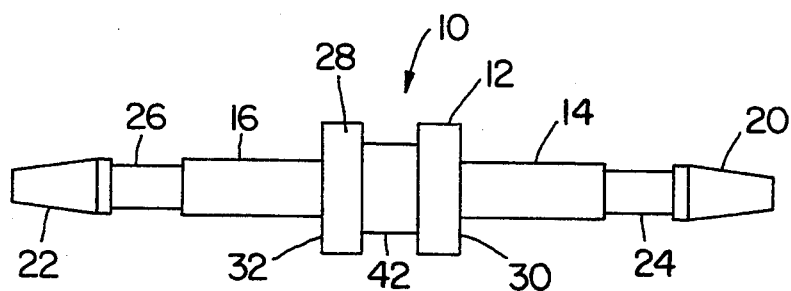
FIG. 3 is a side view of an alternative embodiment of the medical connector of the present invention with the enlarged middle portion having a circumferential suture groove.

FIGS. 3, 4 and 5 illustrate alternative embodiments of the invention. These embodiments are similar to the embodiment of FIGS. 1 and 2 and like reference numerals have been retained where appropriate.

FIG. 3 is a side view of a connector identical to that shown in FIG. 1 with the addition of a circumferential suture groove 42 in the surface 28 of enlarged middle portion 12. If the connector is used without a strain relief sleeve suture groove 42 provides a convenient place at which the catheter may be anchored by suturing it to surrounding tissue.

FIG. 4 is a perspective view of a connector similar to FIG. 1 except that end portions 14 and 16 each include at least one raised circumferential ridge or barb 44. Barbs 44 provide an alternative means for securing the catheter tubing sections to the end portions. Once the end portions are inserted into the tubing sections, barbs 44 tend to restrict the removal of the compliant material of the tubing sections from the end portions.

FIG. 5 illustrates a similar connector except that end portions 14 and 16 are shown with a generally smooth cylindrical surface and with no taper at the ends. The outer surface of end portions 14 and 16 may be roughened to provide a more secure friction fit with the inner surface of the tubing sections.

From the foregoing detailed description of specific embodiments of the invention, it should be apparent that a medical connector and method for its use has been disclosed. Although particular embodiments of the invention have been disclosed herein in detail, this has been done for the purpose of illustration only, and is not intended to be limiting with respect to the scope of the appended claims, which follow. In particular, it is contemplated by the inventors that various substitutions, alterations and modifications may be made to the embodiments of the invention without departing from the spirit and scope of the invention as defined by the claims. For instance, the choice of materials or variations in the shape of the end portions or the enlarged middle portion of the connector are believed to be a matter of routine for a person of ordinary skill in the art with knowledge of the embodiments disclosed herein. Likewise, although the embodiments disclosed relate primarily to use of the connector for connecting catheter sections, the connector could be used for other applications where it is desirable to connect separate sections of medical tubing together, especially those situations where the tubing is to be implanted in the human body. Such applications include connecting sections of stents, penile implants and sphincter implants.

We claim:

1. A connector for medical tubing comprising:
   a first generally cylindrical end portion for insertion in medical tubing,
   a second generally cylindrical end portion for insertion in medical tubing, said first and second end portions each including means for securing the medical tubing to said first and second end portions; and
   an enlarged middle portion lying between said first and second end portions, said enlarged middle portion being generally cylindrical and having a diameter larger than the diameter of said first and second end portions, said enlarged middle portion including a substantially circumferential groove and having a first tubing stop section adjacent said first end portion and a second tubing stop section adjacent said second end portion, said first end portion, said second end portion and said enlarged middle portion defining a central lumen.

2. A method of connecting catheter sections comprising;
   inserting a first end portion of a connector in the first catheter section, said first end portion being substantially cylindrical,
   inserting a second end portion of the connector in a second catheter section, said second end portion being substantially cylindrical, said first and second end portions each including means for securing the medical tubing to said first and second end portions, and
   sliding the first and second end portions into the first and second catheter sections until the sections abut against first and second catheter stop surfaces of an enlarged middle portion of the connector lying between the first and second end portion, said enlarged middle portion being generally cylindrical and having a diameter larger than the diameter of said first and second end portions, said enlarged middle portion further including a substantially circumferentially groove.

3. A connector for medical tubing comprising:
   a first generally cylindrical end portion for insertion in medical tubing;
   a second generally cylindrical end portion for insertion in medical tubing, said first and second end portions each including means for securing the medical tubing to said first and second end portions, said means for securing including at least one circumferentially raised ridge, each said ridge having a substantially equal circumference which is greater than the circumference of said generally cylindrical first and second end portions; and an enlarged middle portion lying between said first and second end portions, said enlarged middle portion being generally cylindrical and having a diameter larger than the diameter if said first and second end portions, said enlarged middle portion having a first tubing stop section adjacent said first end portion and a second tubing stop section adjacent said second end portion, said first end portion, said second end portion and said enlarged middle portion defining a central lumen.

4. A connector for medical tubing comprising:

a first generally cylindrical end portion for insertion in medical tubing;

a second generally cylindrical end portion for insertion in medical tubing, said first and second end portions each including means for securing the medical tubing to said first and second end portions, said means for securing including at least one circumferentially depressed section having a circumference which is less than the circumference of said generally cylindrical first and second end portions; and an enlarged middle portion lying between said first and second end portions, said enlarged middle portion being generally cylindrical and having a diameter larger than the diameter if said first and second end portions, said enlarged middle portion having a first tubing stop section adjacent said first end portion and a second tubing stop section adjacent said second end portion, said first end portion, said second end portion and said enlarged middle portion defining a central lumen.

5. A connector for connecting catheter body sections comprising:

a first end portion for insertion in a catheter body section, said first end portion being substantially cylindrical; and a second end portion for insertion in a catheter body section, said second end portion being substantially cylindrical, said first and second end portions each including means for securing the medical tubing to said first and second end portions, said means for securing including at least one circumferentially raised ridge, each said ridge having a substantially equal circumference which is greater than the circumference of said generally cylindrical first and second end portions, and an enlarged middle portion lying between said first and second end portions, said enlarged middle portion being generally cylindrical and having a diameter larger than the diameter of said first and second end portions, said enlarged middle portion having a first catheter stop section adjacent said first end portion and a second catheter stop section adjacent said second end portion, said first end portion, said second end portion and said enlarged middle portion defining a central lumen substantially parallel to a longitudinal axis of the connector, such that fluids may pass between the catheter body sections through the central lumen.

6. A connector for connecting catheter body sections comprising:

a first end portion for insertion in a catheter body section, said first end portion being substantially cylindrical; and a second end portion for insertion in a catheter body section, said second end portion being substantially cylindrical, said first and second end portions each including means for securing the medical tubing to said first and second end portions, said means for securing including at least one circumferentially depressed section having a circumference which is less than the circumference of said generally cylindrical first and second end portions, and an enlarged middle portion lying between said first and second end portions, said enlarged middle portion being generally cylindrical and having a diameter larger than the diameter of said first and second end portions, said enlarged middle portion having a first catheter stop section adjacent said first end portion and a second catheter stop section adjacent said second end portion, said first end portion, said second end portion and said enlarged middle portion defining a central lumen substantially parallel to a longitudinal axis of the connector, such that fluids may pass between the catheter body sections through the central lumen.

7. A method of connecting catheter sections comprising:

inserting a first end portion of a connector in a first catheter section, said first end portion being substantially cylindrical;

inserting a second end portion of the connector in a second catheter section, said second end portion being substantially cylindrical, said first and second end portions each including means for securing the medical tubing to said first and second end portions, said means for securing including at least one circumferentially raised ridge, each said ridge having a substantially equal circumference which is greater than the circumference of said generally cylindrical first and second end portions; and sliding the first and second end portions into the first and second catheter sections until the sections abut against first and second catheter stop surfaces of an enlarged middle portion of the connector lying between the first and second end portions, said enlarged middle portion being generally cylindrical and having diameter larger than the diameter of said first and second end portions.

8. A method of connecting catheter sections comprising:

inserting a first end portion of a connector in a first catheter section, said first end portion being substantially cylindrical;

inserting a second end portion of the connector in a second catheter section, said second end portion being substantially cylindrical, said first and second end portions each including means for securing the medical tubing to said first and second end portions, said means for securing including at least one circumferentially depressed section having a circumference which is less than the circumference of said generally cylindrical first and second end portions; and sliding the first and second end portions into the first and second catheter sections until the sections abut against first and second catheter stop surfaces of an enlarged middle portion of the connector lying between the first and second end portions, said enlarged middle portion being generally cylindrical and having diameter larger than the diameter of said first and second end portions.

* * * * *